United States Patent [19]
O'Brien

[11] Patent Number: 4,881,811
[45] Date of Patent: Nov. 21, 1989

[54] REMOTE COLOR MEASUREMENT DEVICE

[75] Inventor: John K. O'Brien, Sudbury, Mass.

[73] Assignee: Colorgen, Inc., Billerica, Mass.

[21] Appl. No.: 156,471

[22] Filed: Feb. 16, 1988

[51] Int. Cl.$^4$ .............................. G01J 3/02; G01J 3/08
[52] U.S. Cl. ........................................ 356/323; 356/73;
356/236; 356/446; 356/448; 250/228
[58] Field of Search ............... 356/300, 319, 323, 325,
356/326, 328, 236, 73, 434, 446, 448; 250/227,
226, 228

[56] References Cited

U.S. PATENT DOCUMENTS 4,654,794 3/1987 O'Brien .............................. 356/326

FOREIGN PATENT DOCUMENTS

WO86/03292 5/1986 PCT Int'l Appl. ................. 356/323

Primary Examiner—F. L. Evans
Attorney, Agent, or Firm—Joseph S. Iandiorio

[57] ABSTRACT

A probe, for use with a spectrophotometer, which senses the reflectance of a sample remote from the spectrophotometer. The probe includes a housing having a probe portion positionable proximate the sample, and an integrating chamber disposed within the probe housing and having a radiation input port, a sample port for passing diffused radiation to the sample and returning reflected radiation from the sample, a reference port, and an exit port to receive radiation reflected from the sample through the sample port. The probe further includes a guide for directing radiation to the radiation input port from a radiation source, and an element, responsive to the exit port and the reference port, for selectively conveying reflected radiation from the sample and the wall of the integrating chamber in the probe to the remote spectrophotometer.

22 Claims, 5 Drawing Sheets

REMOTE COLOR MEASUREMENT DEVICE

FIELD OF INVENTION

This invention relates to a remote color measurement probe for use with a spectrophotometer and more particularly to a hand-held probe positionable against a remote sample.

BACKGROUND OF INVENTION

The color of a sample material can be accurately determined using a spectrophotometer. Spectrophotometers include a source of radiation, a device for isolating monochromatic light, and a photoelectric detector. Typically, the sample is illuminated with diffuse light from an integrating sphere which presently is disposed within the spectrophotometer. The integrating sphere receives radiation through an input port from a source such as a tungsten lamp; a reflective material, e.g., barium sulphate, reflects the radiation in multiple reflections to provide uniform diffuse illumination. An exit port is positioned to receive reflected radiation from the sample.

The reflected light is separated into its spectral components to provide reflectance measurements of the sample at each wavelength. Since the color of the sample itself causes a diminution and discoloration of the illumination within the sphere, a reference signal must be provided after the sample is positioned at the sample point. The sphere thus is also provided with a reference port positioned to receive light reflected from the wall of the sphere. Reflected light from the sample is compared to that from the wall to determine the reflectance over a number of wavelengths, e.g., 400–700 nm: the two signals are ratioed over the wavelengths to provide a signal proportional to the sample reflectance.

The device for isolating monochromatic radiation, such as a monochromator, contains a prism or defraction grating which disperses the light into its component wavelengths. The light is passed through an array of photodetectors each of which measures a different narrow frequency band of the radiation dispersed by the monochromator.

There are a number of applications, however, where it is not possible or convenient to position the sample at the sample port of the integrating sphere within the spectrophotometer. In the area of dentistry, people require replacement teeth for one or more of their natural teeth. Presently, a dentist attempts to match the characteristics of the natural tooth using shade guides which are tooth-shaped plastic or ceramic pieces attached to a short handle. The dentist visually compares the color of the tooth with different shade guides until an optimum match is obtained. The dentist then provides the guide number of the optimum shade guide to the technician who produces the replacement tooth using a formulation related to that guide number.

However, the guides do not cover the complete range of shades encompassed by natural teeth. The guides are not structured in a systematic way, e.g., the Munsell color order system which categorizes a color based on its hue, value and chroma. Further, natural teeth have a translucency and fluorescence which the replacement teeth rarely replicate. Moreover, the initial color measurement of the tooth is estimated visually rather than quantitatively measured by instrument. The type of illumination within the room, partial color blindness of some dentists, and other factors often diminish color quality of the restoration.

Other applications of color measurement include paint matching. Even if a customer knows the original formulation of the paint applied to a surface such as an interior wall, degradation over time fades the paint so that the original formulation no longer matches the present condition of the paint. Presently, a sample of the point must be physically removed from the wall to be analyzed by a spectrophotometer.

SUMMARY OF INVENTION

It is therefore an object of this invention to provide a probe for sensing the reflectance of a sample remote from a spectrophotometer.

It is a further object of this invention to provide such a probe which enables the spectrophotometer to measure the color of the remote sample.

It is a further object of this invention to provide such a probe which can be hand-held.

Yet another object of this invention is to provide such a probe which is as accurate as conventional dual-beam spectrophotometers.

It is a further object of this invention to provide such a probe which can measure the reflectance including translucency and fluorescence characteristics of natural teeth.

It is a further object of this invention to provide such a probe which can measure the transmission characteristics of a living tooth.

This invention features a probe for sensing the reflectance of a sample remote from a spectrophotometer and conducting reflected radiation to the spectrophotometer. There are a probe housing having a probe portion positionable proximate the sample and an integrating chamber disposed within the housing. The integrating chamber includes a radiation input port, a sample port for passing diffused radiation to the sample and returning reflected radiation from the sample, a reference port, and an exit port to receive radiation reflected from the sample to the sample port. The probe further includes a guide for directing radiation to the radiation input port from a radiation source and means for selectively conveying reflected radiation from the sample, as provided through the exit port, and from the wall of the integrating chamber, as provided through the reference port; the radiation from the sample and the wall is selectively conveyed to the remote spectrophotometer.

In one embodiment, the sample port includes a passage extending between the integrating chamber and the outer surface of the probe portion, and the probe portion is tapered toward the passage. The integrating chamber includes a baffle coated with reflective material and positioned proximate the radiation input port to assist diffusion within the integrating chamber of radiation from the source. The integrating chamber is spherical.

In another embodiment, the means for selectively conveying includes mirror means and means for realigning the mirror means relative to the reference port and the exit port. The means for realigning may include solenoid means connected to the mirror means, and the exit port includes an aperture stop for directing reflected radiation onto the mirror means. The means for selectively conveying further includes a radiation guide segment for conducting radiation from the reference point to the mirror means. The mirror means is disposed within the housing and the housing includes a mirror chamber for accommodating the mirror means. The means for selectively conveying includes a reflected radiation guide for conducting radiation from the sample and the wall to the spectrophotometer, and the housing includes a handle portion graspable by a human hand.

In yet another embodiment, the probe further includes an extension for directing radiation through a sample into the sample port. There are also means for selectively switching radiation in the guide to the extension to accomplish transmission through the sample.

DISCLOSURE OF PREFERRED EMBODIMENT

Other objects, features and advantages will occur from the following description of a preferred embodiment and the accompanying drawings, in which.

Figure 1:
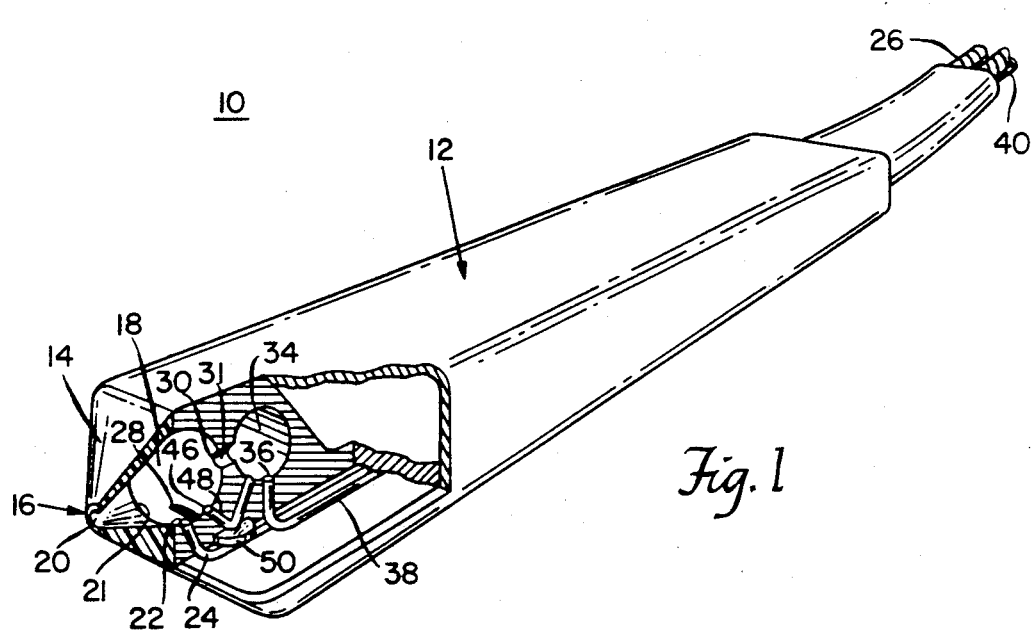
FIG. 1 is an axonometric, partial cutaway view of a probe according to this invention.
Figure 2:
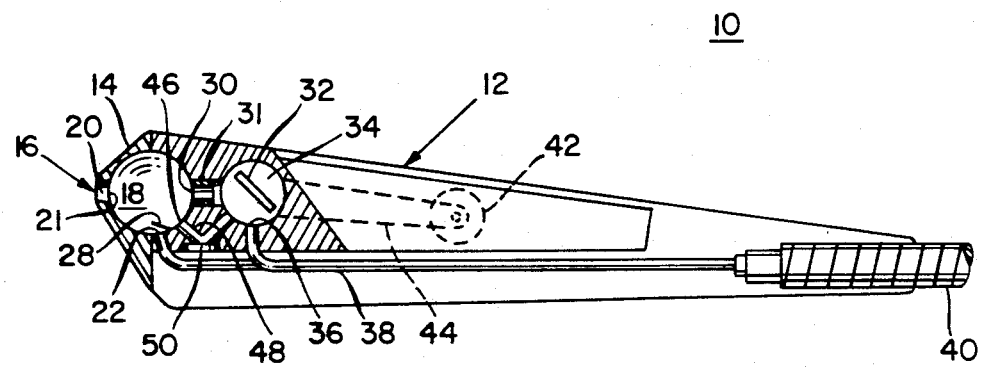
FIG. 2 is an elevational cross-sectional view of the probe of FIG. 1.

There is shown in FIGS. 1 and 2 probe 10 according to this invention having housing 12 with probe portion 14. When the reflectance of a portion of the human body is to be measured, particularly for dental applications, probe portion 14 is a tapered plastic nose. In another construction, all of housing 12 including portion 14 is fabricated from metal such as aluminum.

The tapered nose of portion 14 enhances visual alignment of probe 10 with the sample to be measured. The sample is placed against sample port 16 which is responsive to integrating chamber 18 through passage 20. Passage 20 is a channel of white nylon or Teflon which promotes the transfer of radiation to and from the sample. The interior portion of passage 20 is defined by bevelled rim 21 of sample port 16; bevelled rim 21 increases the amount of radiation admitted to the sample. Incoming radiation from a radiation source is provided through radiation input port 22 through radiation guide 24 such as a fiber optic wave guide or liquid light guide. Radiation from a radiation source (not shown) is provided through radiation guide 24 within protective sheathing 26. Radiation enters through input port 22 and strikes baffle 28, which is coated with barium sulfate to enhance diffusion of the radiation about integrating chamber 18. Radiation returned from the sample passes through aperture 31 of exit port 30 to strike mirror 32, FIG. 2, within mirror chamber 34. Alternatively, a lens or light guide segment replaces aperture 31 to direct reflected radiation onto sample mirror 32. In this construction integrating chamber 18 is spherical while mirror chamber 34 is cylindrical. Reflected radiation then travels through output port 36 to radiation guide 38, which exits housing 12 through protective sheathing 40 and conducts radiation to the spectrophotometer. Alternately, mirror 32 is realigned by bidirectional electric motor 42 and belt 44, both shown in phantom in FIG. 2. After mirror 32 is realigned, radiation passes through reference port 46 and then through radiation guide segment 48 which includes mirror 50.

Figure 3A:
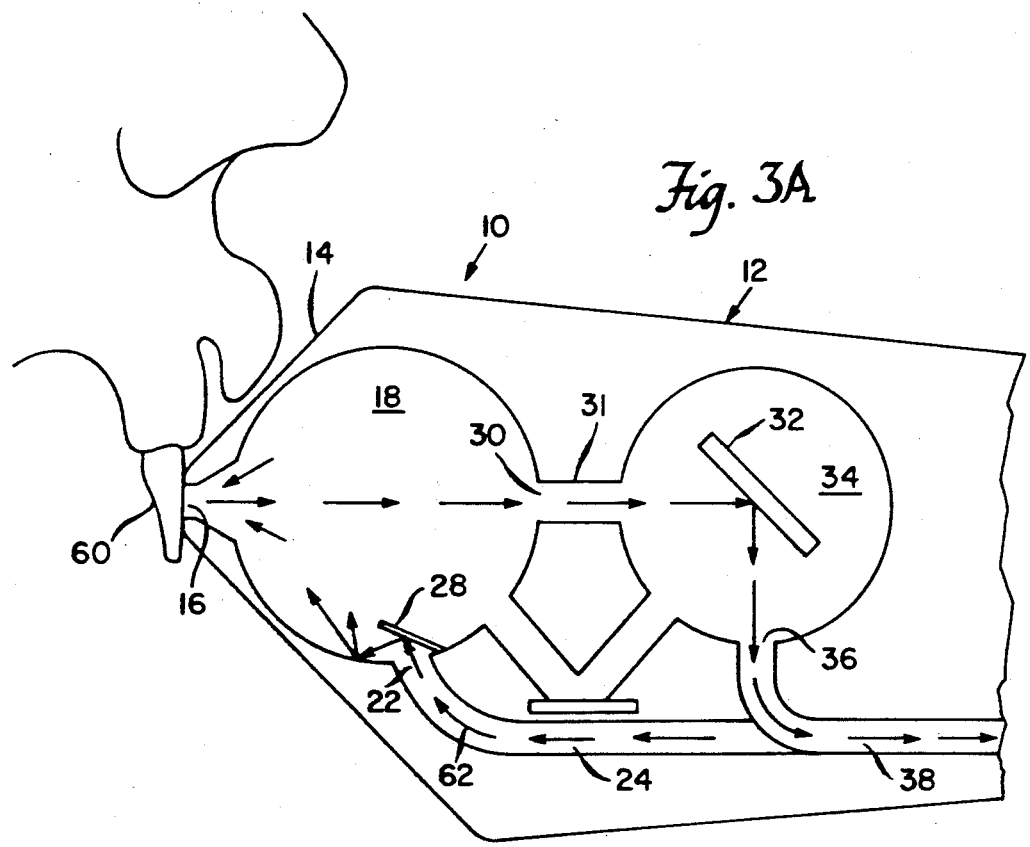
FIG. 3A is a schematic diagram showing the path of reflected light from a tooth.
Figure 3B:
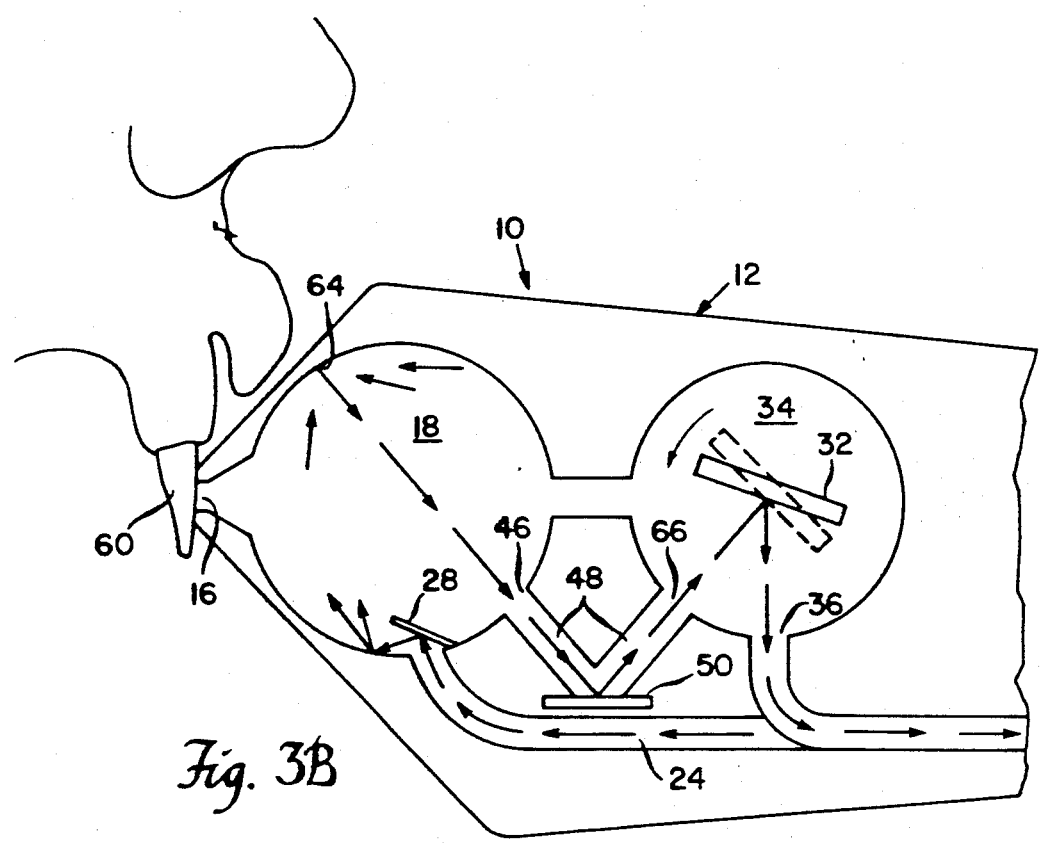
FIG. 3B is a schematic diagram showing the path of diffuse radiation reflected from the wall of the integrating sphere to a spectrophotometer.

The operation of probe 10 is shown in FIGS. 3A and 3B. Sample port 16 is positioned against tooth 60 whose color is to be matched. Incoming radiation 62 through guide 24 strikes baffle 28 and is reflected about integrating sphere 18. Diffused radiation strikes tooth 60 and passes through exit port 30 and aperture stop 31 which restricts the cone of reflected light from the sample and directs it onto switching mirror 32. Radiation then passes through output port 36 of mirror chamber 34 and is conveyed through radiation guide 38 to the spectrophotometer. A dark sample is then taken, that is, a reading is taken by the spectrophotometer without sampling radiation through guide 38.

With sample port 16 still positioned against tooth 60, radiation is again provided through guide 24 and radiation reflected off wall 64 is sampled through reference port 46. The reflected radiation travels through radiation guide segment 48, is reflected off plane mirror 50, and is provided through reference input port 66 to mirror chamber 34. Mirror 32 is shown in its second position so that it directs radiation from reference input port 66 to output port 36.

Figure 4A:
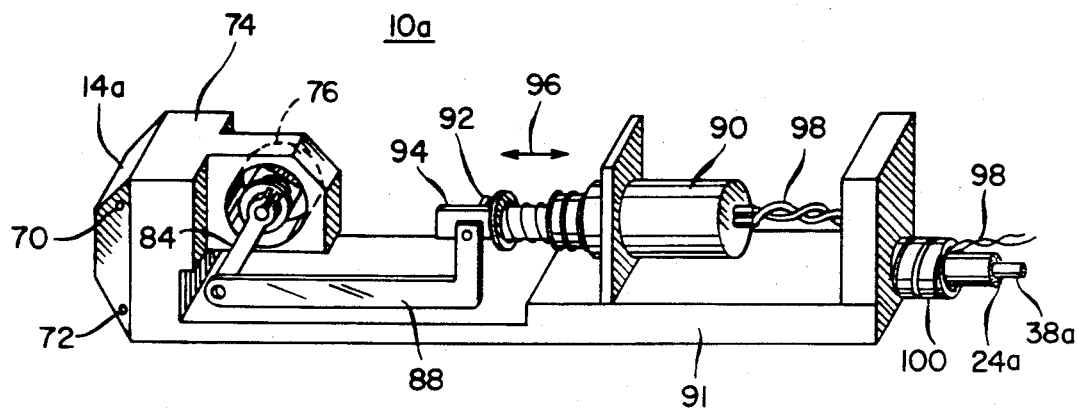
FIG. 4A is a partial diagram of an alternative probe having a solenoid arrangement for positioning the switching mirror assembly.
Figure 4B:
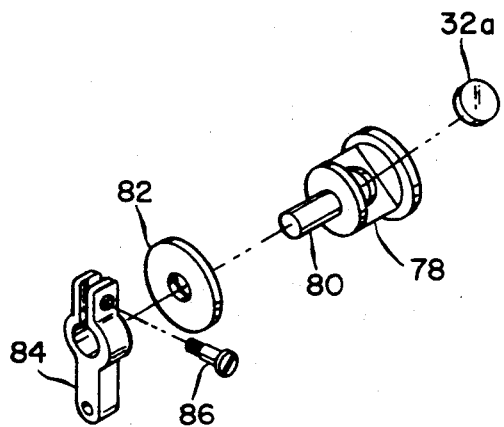
FIG. 4B is an exploded, more detailed view of the switching mirror assembly of FIG. 4A.

Probe 10a, FIG. 4A, is another construction of a probe according to this invention. Removable nose cone 14a is attached through screw holes 70, 72 to support 74 which includes the integrating chamber (not shown) and mirror chamber 76 (shown in phantom). As shown in FIG. 4B, mirror 32a is disposed in drum 78. Shaft 80 passes through washer 82 and is secured to lever arm 84 by screw 86. Lever arm 84 is in turn secured to linkage 88, FIG. 4A, to solenoid 90. Pin 92 secures linkage 88 to shaft 94 of solenoid 90 which is movable from an extended to a retracted position as indicated by arrow 96. Solenoid 90 is mounted on base 91 and is powered through electric wires 98 which are carried within protective sheathing 100. Sheathing 100 also contains coaxial radiation guides 24a and 38a for respectively conveying radiation to and from probe 10a.

Figure 5:
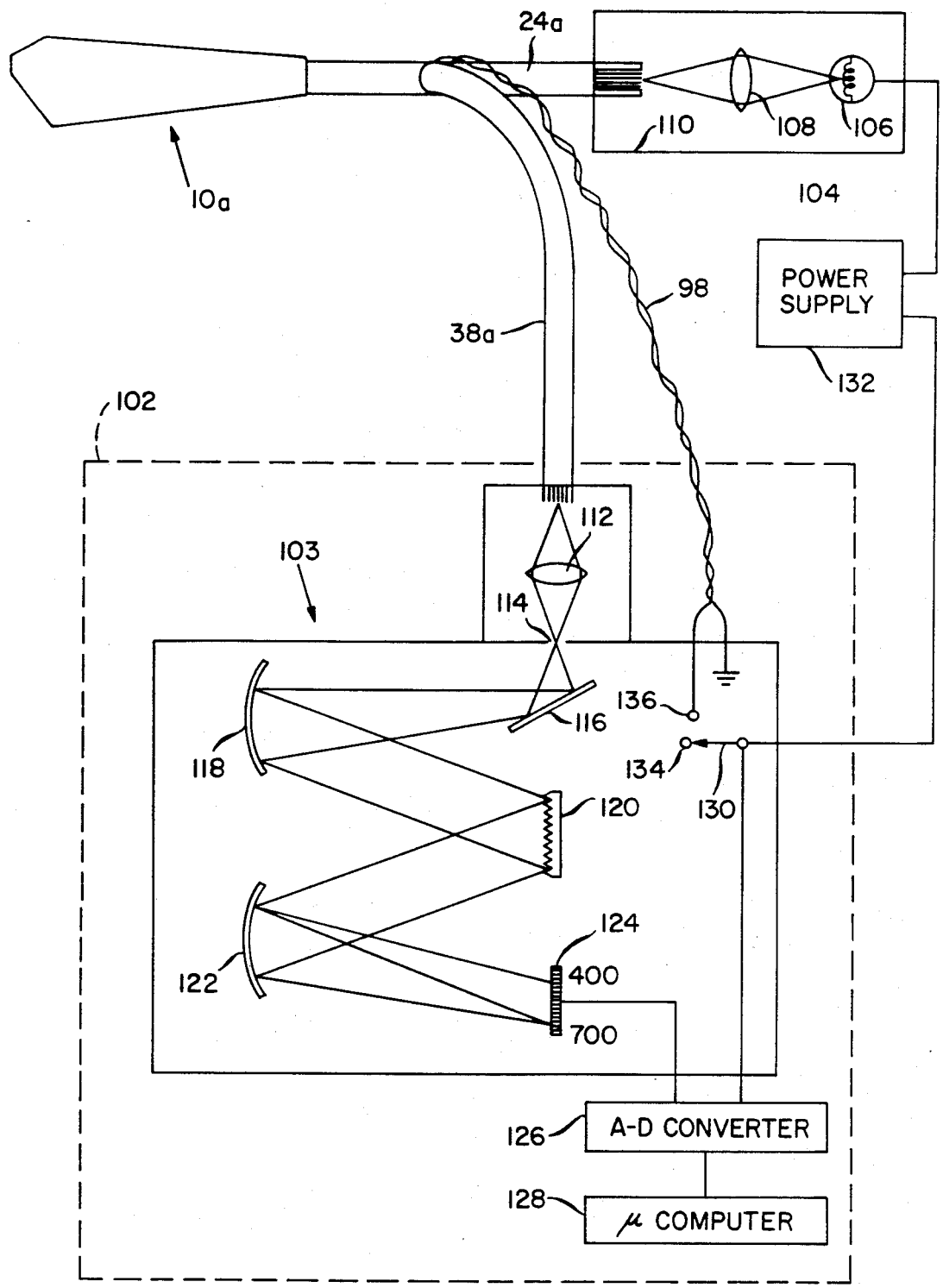
FIG. 5 is a schematic diagram of the probe of FIG. 4A in combination with a spectrophotometer.

Probe 10a is shown connected to spectrophotometer 102, FIG. 5, and radiation source 104 through radiation guides 58a and 24a, respectively. Radiation source 104 includes lamp 106 and lens 108 within lamp housing 110. Lens 108 directs source radiation into radiation guide 24a; the reflected light is then returned through radiation guide 38a as described above and is directed by lens 112 through slit 114 of polychromator 103. Mirror 116 and collimating mirror 118 direct the light to diffraction grating 120. Diffraction grating 120 separates the light into its component wavelengths. The dispersed light between, e.g., 400 and 700 nm, is then focussed by focussing mirror 122 onto detector 124 such as a photodiode array. Signals from polychrometer 103 are provided through A/D converter 126 to microcomputer 128.

The switching mirror within probe 10a is controlled by microcomputer 128 through switch 130. Power from power supply 132 is directed from open point 134 to terminal 136 of wires 98 to energize the solenoid within probe 10a when sampling of the wall of the integrating chamber is desired.

Figure 6:
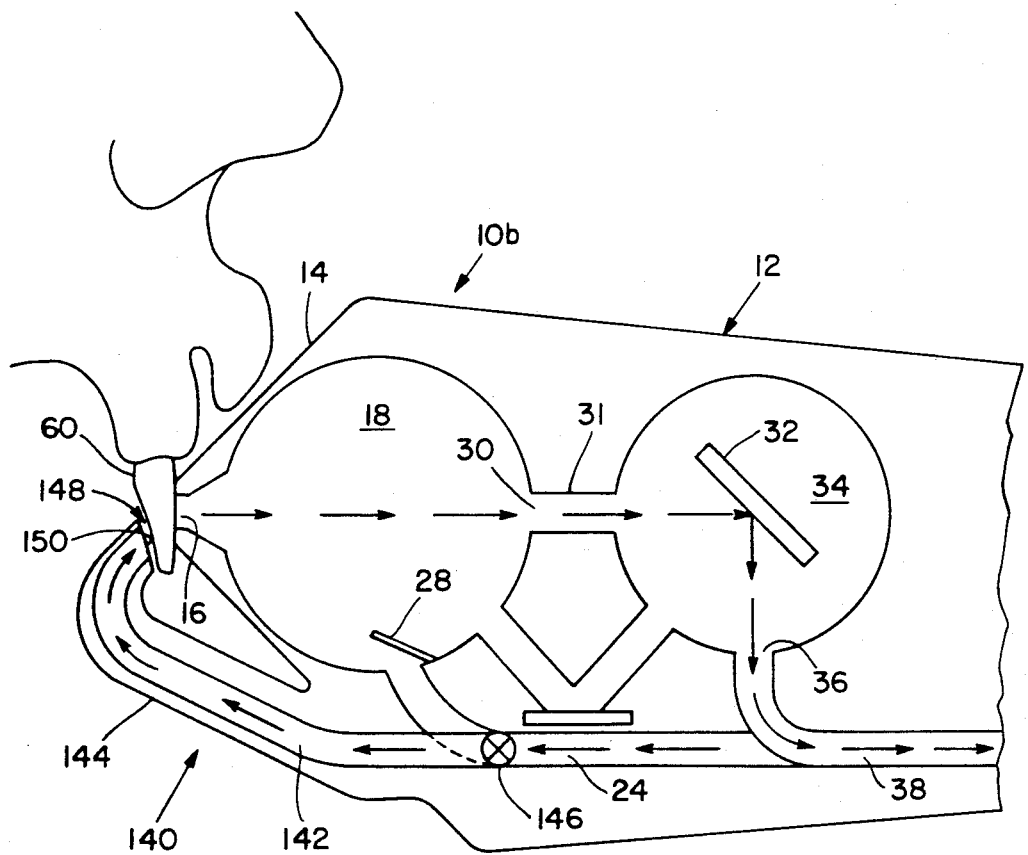
FIG. 6 is a schematic diagram of an alternative probe according to this invention for measuring transmission of a tooth.

Probe 10b, FIG. 6, utilizes extension 140 to measure the transmission characteristics of tooth 60. Extension 140 includes fiber optic guide 142 within housing 144. Fiber optic guide 142 is connected to fiber optic guide 24 through switch 146. Tooth 60 is received in gap 148 and is positioned against sample port 16. Extension 140 is constructed of a flexible material so that end 150 of fiber optic guide 142 rests against the back of tooth 60. Alternatively, a pivot and grip are provided to allow manual clamping of end 150 against tooth 60.

In operation, a calibration chip is placed within gap 148 and a transmission reading is taken through the calibration chip. The calibration chip is removed and probe 10b is positioned to receive tooth 60 within gap 148. If desired, reflectance measurements can then be conducted by operating switch 146 to illuminate sphere 18 as described above.

Although specific features of the invention are shown in some drawings and not others this is for convenience only as each feature may be combined with any or all of the other features in accordance with the invention.

Other embodiments will occur to those skilled in the art and are within the following claims:

What is claimed is:

1. A probe, for use with a spectrophotometer, for sensing the reflectance of a sample remote from the spectrophotometer, comprising:
   A probe housing having a probe portion positionable proximate the sample;
   an integrating chamber for diffusing radiation disposed within said probe housing and having a radiation input port for providing radiation to said integrating chamber, a sample port for passing diffused radiation to the sample and returning reflected radiation from the sample, a reference port for receiving diffused radiation directly from the chamber, and an exit port to receive radiation reflected from the sample through said sample port;
   an output port for receiving reflected sample radiation from said sample and diffused radiation directly from the chamber and for transmitting the received radiation to the remote spectrophotometer;
   a guide for directing radiation to said radiation input port from a radiation source; and
   means for selectively directing the diffused radiation from the chamber through said reference port and the radiation reflected from the sample through said exit port to said output port.

2. The probe of claim 1 in which said sample port includes a passage extending between said integrating chamber and the outer surface of said probe portion.

3. The probe of claim 2 in which said probe portion is tapered toward said passage.

4. The probe of claim 1 in which said integrating chamber includes a baffle positioned proximate said radiation input port to assist diffusion within said integrating chamber of radiation from said source.

5. The probe of claim 4 in which said baffle is coated with reflective material.

6. The probe of claim 1 in which said integrating chamber is spherical.

7. The probe of claim 1 in which said means for selectively directing includes mirror means and means for realigning said mirror means relative to said reference port and said exit port.

8. The probe of claim 7 in which said means for realigning includes solenoid means connected to said mirror means.

9. The probe of claim 7 in which said exit port includes an aperture stop for directing reflected radiation onto said mirror means.

10. The probe of claim 7 in which said means for selectively directing further includes a radiation guide segment for conducting radiation from said reference port to said mirror means.

11. The probe of claim 7 in which said mirror means is disposed within said housing.

12. The probe of claim 11 in which said housing includes a mirror chamber for accommodating said mirror means.

13. The probe of claim 1 in which said means for selectively directing includes a reflected radiation guide for conducting radiation from the sample and a wall of the integrating chamber to the spectrophotometer.

14. The probe of claim 1 in which said housing includes a handle portion graspable by a human hand.

15. The probe of claim 1 further including an extension for directing radiation through the sample into said sample port, said extension defining a gap between it and said sample port in which the sample is positionable.

16. The probe of claim 15 further including means for selectively switching radiation in said guide from said radiation source to said extension.

17. A probe, for use with a spectrophotometer, for sensing the reflectance of a sample remote from the spectrophotometer, comprising:
   a probe housing having a probe portion positionable proximate the sample;
   an integrating chamber for diffusing radiation disposed within said probe housing and having a radiation input port for providing radiation to said chamber, a sample port for passing diffused radiation to the sample and returning reflected radiation from the sample, a reference port for receiving diffused radiation directly from said chamber, and an exit port to receive radiation reflected from the sample through said sample port;
   an output port for receiving reflected radiation from said sample and diffused radiation from the chamber and for transmitting the received radiation to the remote spectrophotometer;
   a guide for directing radiation to said radiation input port from a radiation source; and
   means for selectively conveying reflected radiation from the sample and from a wall of the integrating chamber in the probe to the remote spectrophotometer through a reflected-radiation guide, said means for selectively conveying including mirror means and means for realigning said mirror means relative to said exit portion and said reference port to selectively provide reflected radiation from the sample and the wall to said reflected-radiation guide.

18. A probe for use with a spectrophotometer for sensing the reflectance of a sample remote from the spectrophotometer, said probe comprising:
   a probe housing having a probe portion positionable proximate the sample;
   a source of input radiation;
   an integration chamber disposed within said probe housing for receiving and diffusing said input radiation;

a sample port for delivering diffused input radiation to said sample;
an output port; and
means for selectively directing to said output port said diffused input radiation reflected from said sample and the diffused input radiation reflected directly from said integration chamber.

19. The probe of claim 18 in which said means for selectively directing includes mirror means and means for realigning said mirror means relative to radiation reflected from said sample and diffused radiation from said integration chamber.

20. The probe of claim 19 in which said means for directing includes an exit port for passing radiation reflected from said sample to said mirror means.

21. The probe of claim 19 in which said means for directing includes a reference port for receiving and directing diffused radiation from the chamber to said mirror means.

22. The probe of claim 21 in which said means for selectively directing further includes a radiation guide segment for conducting radiation from said reference port to said mirror means.

* * * * *